United States Patent
De Craecker

(10) Patent No.: US 6,609,413 B1
(45) Date of Patent: Aug. 26, 2003

(54) METHOD AND APPARATUS FOR MEASURING CETANE NUMBER OF DIESEL FUEL

(75) Inventor: Roger De Craecker, Beersel (BE)

(73) Assignee: ATOFINA Research, S.A., Seneffe (BE)

( * ) Notice: Subject to any disclaimer, the term of this patent is extended or adjusted under 35 U.S.C. 154(b) by 0 days.

(21) Appl. No.: 09/631,340

(22) Filed: Aug. 2, 2000

(30) Foreign Application Priority Data

Aug. 5, 1999  (EP) .......................................... 99115525

(51) Int. Cl.⁷ ............................................. G01N 33/22
(52) U.S. Cl. ..................................................... 73/35.02
(58) Field of Search ...................... 73/35.02; 123/198 A

(56) References Cited

U.S. PATENT DOCUMENTS 5,457,985 A * 10/1995 Cellier et al. ............... 73/35.02
6,026,778 A *  2/2000 Mille et al. ................. 73/35.02

FOREIGN PATENT DOCUMENTS

| EP | 0895080 |   | 2/1999 |          |
|----|---------|---|--------|----------|
| GB | 2163878 | * | 8/1985 | G05D/21/02 |
| GB | 2163878 |   | 3/1986 |          |

* cited by examiner

Primary Examiner—Hezron Williams
Assistant Examiner—Maurice Stevens
(74) Attorney, Agent, or Firm—William D. Jackson

(57) ABSTRACT

A method of continually measuring the cetane number of a diesel fuel, the method comprising the steps of:

(a) providing a diesel engine having means for selectively supplying at least three diesel fuels to the engine, a first actuator for varying the injection timing of the engine, a second actuator for varying the fuel flow of the engine, and a third actuator for varying the compression ratio of the engine;

(b) providing a first supply of a diesel fuel of known cetane number, a second supply of a diesel fuel of different known cetane number and a third supply of a diesel fuel of unknown cetane number to be measured, the third supply being connected to a diesel fuel blending system;

(c) in a first cycle selectively and alternately supplying the first, second and third supplies to the diesel engine, and for each supply, controlling the first actuator to achieve an injection timing of a predetermined angle before top dead centre, controlling the second actuator to achieve a predetermined fuel flow and controlling the third actuator to achieve a predetermined diesel fuel ignition delay by varying the compression ratio of the engine;

(d) determining the cetane number of the third supply by linear interpolation of the pre-chamber plug positions, corresponding with the respective compression ratio values, for the three supplies; and (e) periodically repeating steps (c) and (d) in further cycles to yield a series of cetane number values of the third supply.

20 Claims, 8 Drawing Sheets

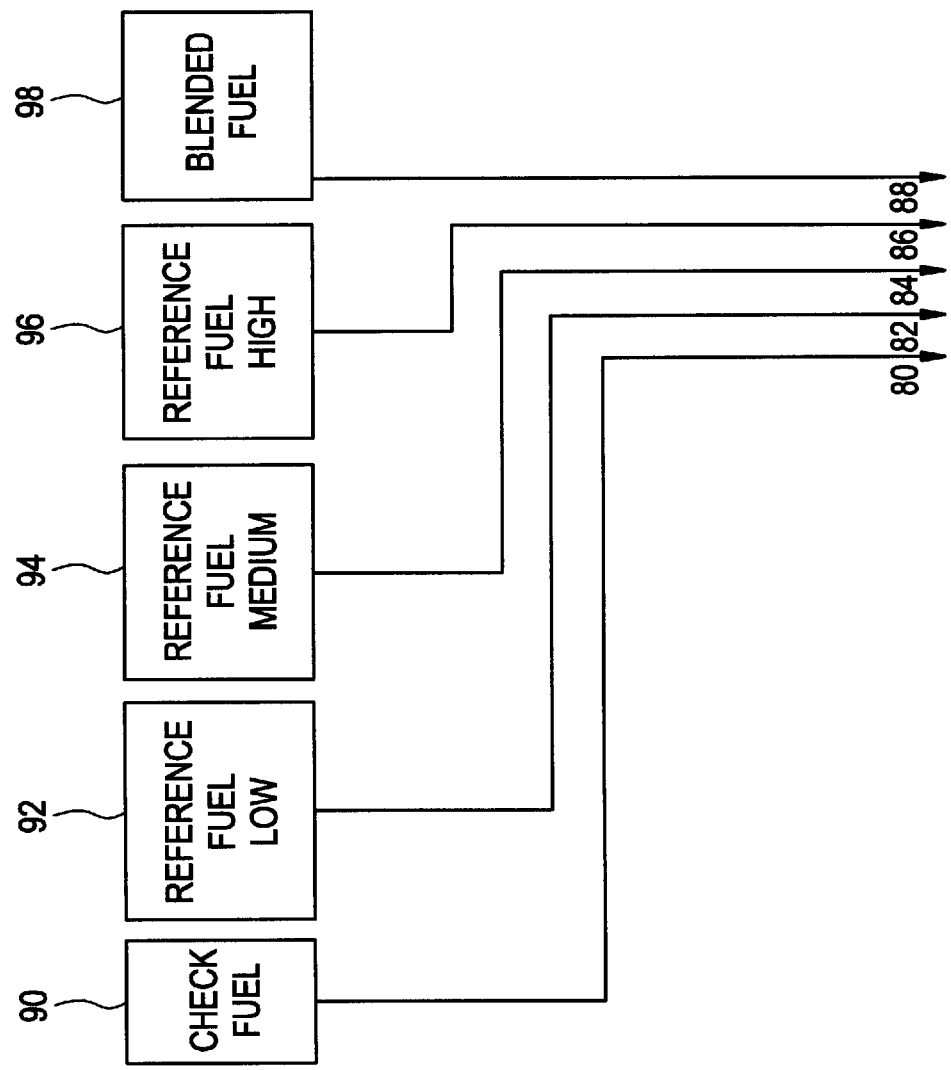

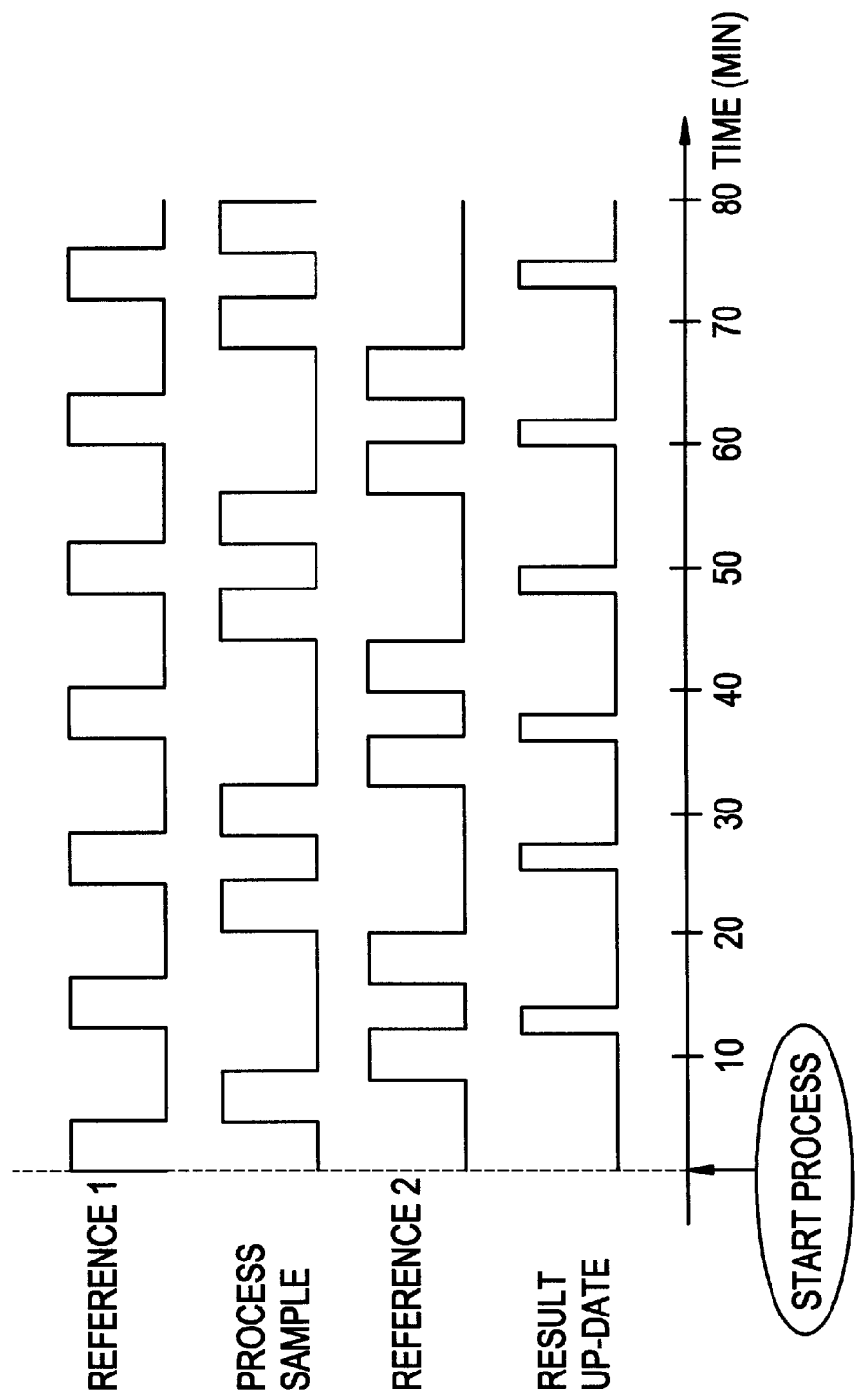

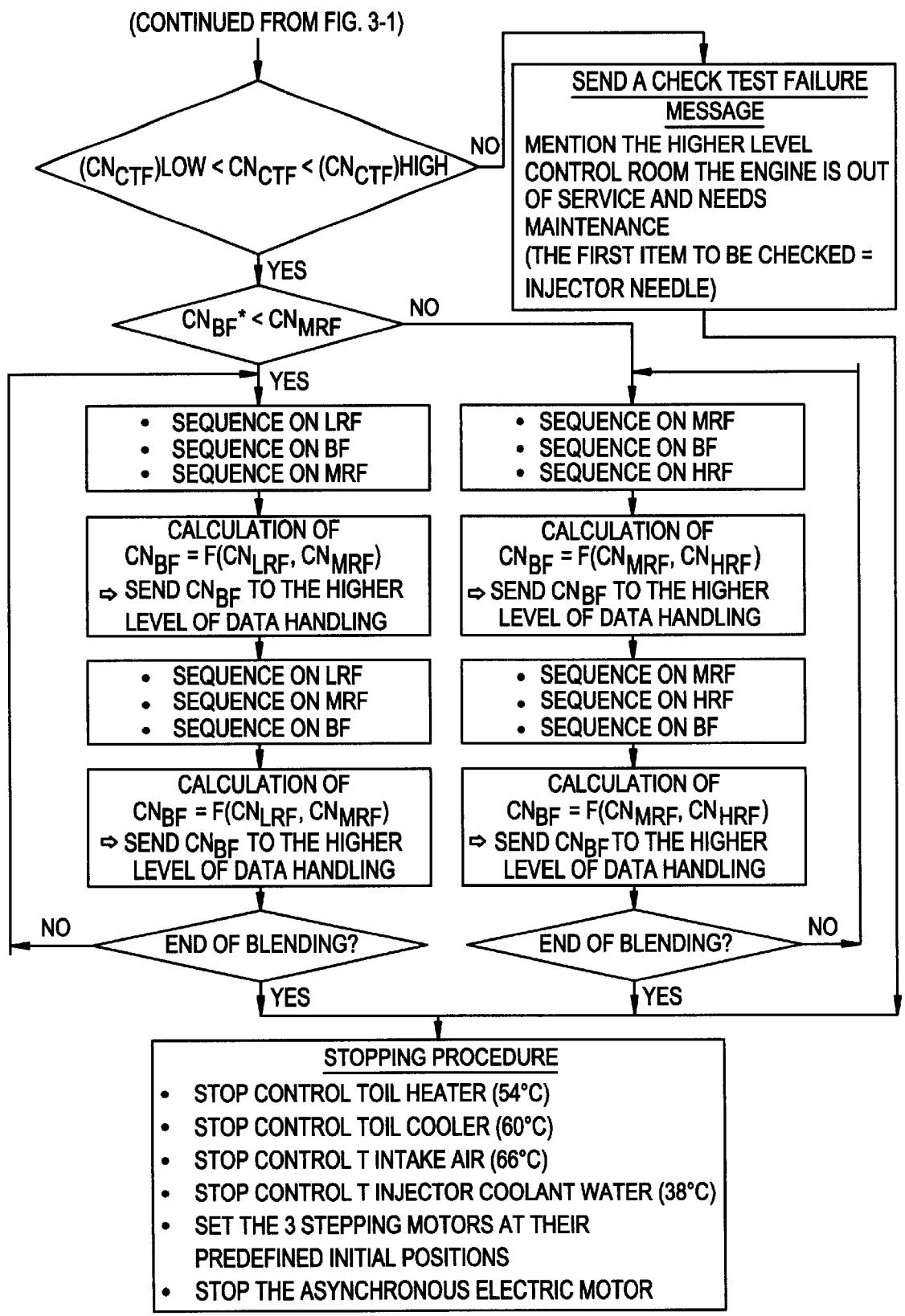

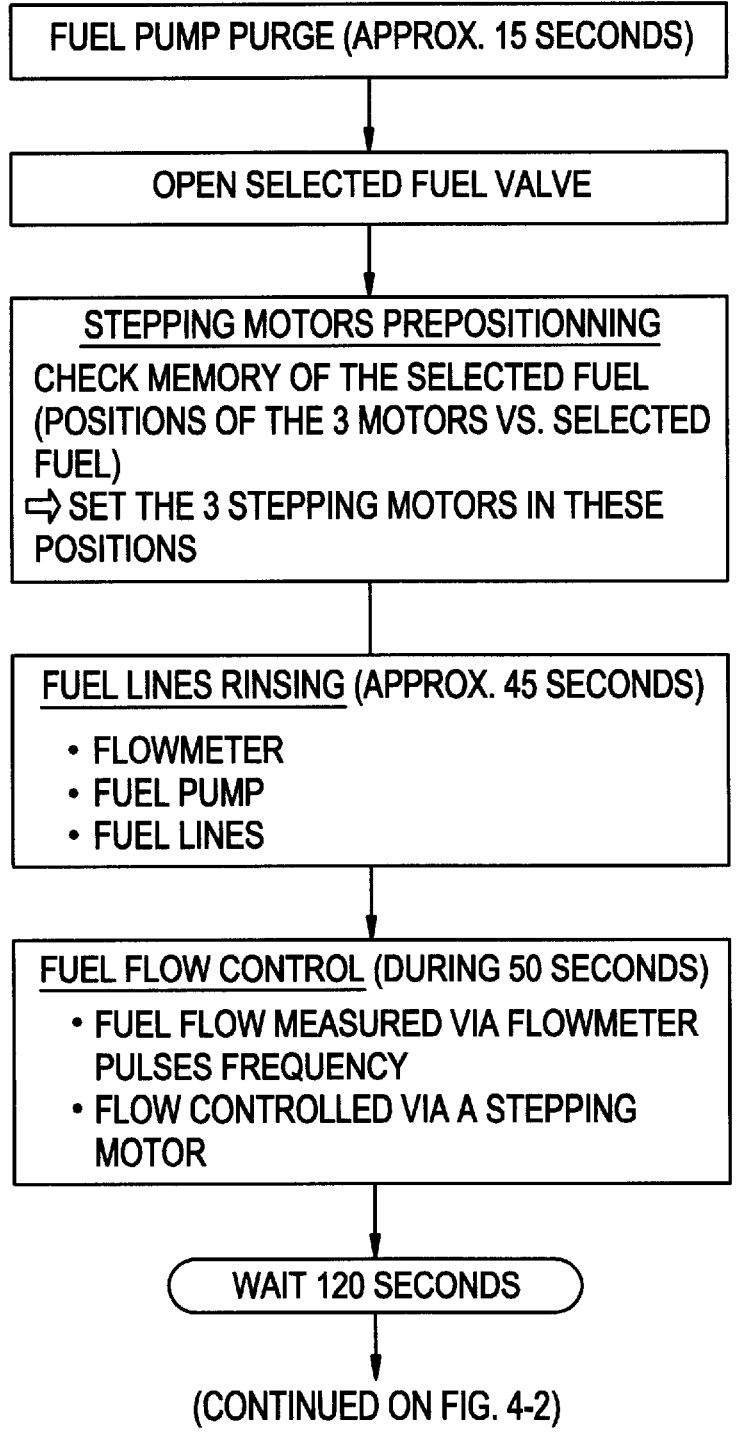

METHOD AND APPARATUS FOR MEASURING CETANE NUMBER OF DIESEL FUEL

BACKGROUND TO THE INVENTION

The present invention relates to a method of and an apparatus for measuring the cetane number of a diesel fuel.

DESCRIPTION OF THE PRIOR ART

Diesel fuels (otherwise known as gasoils) are designated with a cetane number (CN) which is an indication of the readiness of the diesel fuel to ignite when injected into the compressed air in the combustion chamber of a diesel engine. The higher the cetane number, the quicker is the ignition which follows the injection. Thus the cetane number is a characteristic of the self-ignition quality of the diesel fuel.

The cetane number is currently determined internationally by the procedure specified in ASTM D-613. This test is required to be manually performed on a sample of a finished blend of diesel fuel using a single cylinder four stroke diesel engine, having a variable compression ratio. The test requires a manual and critical adjustment of the quantity of injected fuel, as well as the injection timing and the compression ratio of the engine, in order to produce a constant ignition delay corresponding to a crank angle of 13°, (i.e. a delay of from 13° before top dead centre to top dead centre). The test is performed on the finished blend sample, as well as on reference fuels having known cetane number, which are available from Phillips Petroleum of Bartlesville, Okla., USA. The cetane number of the finished blend sample is determined by a linear interpolation of the pre-chamber compression plug position found for the blended fuel, as compared to the corresponding positions for the reference fuels. This manual test lasts about one hour and is required to be performed on a sample of diesel fuel after blending. Thus the cetane number is only measured when the blending operation has been completed, thus preventing correction of the formulation of the diesel fuel blend on-line in the refinery.

Most importantly, the manual test also has poor precision. Although historically there has been much research worldwide to improve the inaccurate procedure of ASTM D-613, the repeatability of the test is as high as 0.9 cetane points and the reproducibility of the test is as high as 3.9 cetane points. No alternative test standard is accepted today, for example by the European Committee for Standardisation (CEN). Accordingly, the ASTM D-613 standard is likely to be in use for several years.

There are increasing commercial and technical requirements for cetane number determination to be accurately and reliably achievable. There is also an increasing demand for the cetane number to be determined on-line in the diesel fuel blending system. The cetane number has been included in the European diesel fuel specification EN590 specified by the European Committee for Standardisation. Since Oct. 1st, 1996 the cetane number has been required under EN590 to be at least 49 and the cetane number will need to be a minimum of 51 from Oct. 1st, 2000. It is likely that the diesel fuel standards will require increasingly higher cetane numbers in the future. The cetane number of the diesel fuel needs to be certified by the refiner. These increasingly higher requirements for the cetane number of diesel fuels will tend to force diesel fuel refiners to put commercially more valuable refinery streams and cetane improver additives into diesel fuel. This will make diesel fuel more expensive.

There is thus a need for refiners to be able to measure the cetane number of diesel fuels accurately and continuously on-line in the blending system so that a particular target threshold for the cetane value to meet the required standard can be achieved during the blending process without unnecessarily increasing the cetane number over the target threshold which constitutes a "give-away" of cetane number which is not commercially recoverable by the refiner. Currently, using the manual testing of finished blends, the blends can be found to be out of specification or can give-away cetane number, leading to significant loss of commercial value, and of time which is required for re-blending and re-testing of the fuel.

There have been prior proposals for the automatic on-line determination of cetane number in a CFR (Committee of Fuel Research) engine which is the engine specified in ASTM D-613.

Thus EP-A-0610118 discloses such a method which operates the CFR engine at constant compression ratio and compares the measured ignition delay of the blend sample with those of two reference fuels. Since this automatic process is an over-simplification of the process required by the ASTM D-613 standard, and in contrast to the standard does not have a constant ignition delay, this automatic process may not be used for product certification in accordance with that standard.

WO-A-97/39349 discloses an automated method which also requires the CFR engine to operate at constant compression ratio and compares the measured ignition delay of the blend sample with that of one reference fuel. The difference in ignition delay between the two fuels is employed to calculate a difference in cetane number, based on the calibration of the engine with two known reference fuels, once at the start of blending. Both the blend sample and the reference fuel have their own injection pump, which are each adjusted for flow and timing of the injection, the adjustment being at the start of blending. The cetane number determination is fed back to the adjustment of the components of the diesel fuel, and the mixture of cetane improver additives. Again, as this process is an over-simplification of the process specified in the ASTM D-613 standard, and does not have a constant ignition delay, it may not be used for product certification.

EP-A-0895080 also discloses a method of measuring cetane number of a diesel fuel in which the cetane number of a reference fuel is calculated using the difference between the average values of the ignition delay of the fuel to be measured and the reference fuel.

GB-A-2163878 discloses a process and device for adjusting the cetane rating of gasoil produced in a refinery. Again, during the measurement phase the compression ratio is maintained at a constant value.

U.S. Pat. No. 5,457,985 also discloses a process for measuring the cetane number of supply fuels for diesel engines which measures an autoignition delay of a diesel engine operating at constant speed with a constant volume compression ratio.

It has also been proposed to measure the cetane number of diesel fuels continuously by measuring the infra-red spectrum of the blended fuel and calculating the cetane number from algorithms based on a Fourier transform analysis. However, such calculation methods have a lower accuracy than the standard CFR methods discussed above.

There is a standard ASTM D-2885 for the on-line automatic measurement of the octane number of gasoline which is used by refineries during the gasoline blending process.

The test procedure is based on an automated CFR octane engine, which compares the blend header gasoline with "prototype fuels". Such prototype fuels are themselves periodically compared with "standard fuels", which have been separately tested (by "round robin" testing by a number of different refiners in the petroleum industry) in at least sixteen manual CFR engines. Such a process has been considered to have a better accuracy than manual determination, due to the use of the average octane number of the standard fuels which have been tested in "round robin" testing, and equally due to the large number of repetitions of the comparative measurement of the blend header octane number with that of the "prototype" fuels. Installations embodying this procedure are currently used all over the world. However, there is no such corresponding automatic cetane number determination process using the CFR engines meeting the parallel ASTM D-613 standard for the cetane number of diesel fuel.

SUMMARY OF THE INVENTION

In summary, there is a need in the art for a method of and apparatus for determining cetane number of diesel fuels which enables the on-line measurement of cetane number permitting certification of the cetane number of a batch of diesel fuel in accordance with accepted International standards, for example There is also a need in the art for such a method and apparatus which enable cetane numbers to be determined not only automatically on-line but also with high accuracy, repeatability and reproducibility.

There is further a need in the art for such a method and apparatus which enable the cetane number of a diesel fuel to be controlled during blending to permit a target cetane value to be achieved reliably.

There is a yet further need in the art for a method and apparatus which can be readily integrated into a diesel fuel blending process and system to enable the cetane number of the blended diesel fuel to be controlled continuously.

The present invention aims at least partially to meet these needs.

Thus it is object of the present invention to provide a method of and an apparatus for determining the cetane number of a diesel fuel which are integratable into a diesel fuel blending system in a refinery for continuously determining the cetane number of the blend measured in accordance with an accepted standard.

It is a further object of the present invention to provide such a method and apparatus which can enable a continuously determined cetane number to be inputted into a control system for a diesel fuel blending system in a refinery to permit optimisation of the blend to achieve the objective of having the diesel fuel within the full specification with the least expensive blending additives and components available in the blend system.

Accordingly, the present invention provides a method of continually measuring the cetane number of a diesel fuel, the method comprising the steps of:
 (a) providing a diesel engine having means for selectively supplying at least three diesel fuels to the engine, a first actuator for varying the injection timing of the engine, a second actuator for varying the fuel flow of the engine, and a third actuator for varying the compression ratio of the engine;
 (b) providing a first supply of a diesel fuel of known cetane number, a second supply of a diesel fuel of different known cetane number and a third supply of a diesel fuel of unknown cetane number to be measured, the third supply being connected to a diesel fuel blending system;
 (c) in a first cycle selectively and alternately supplying the first, second and third supplies to the diesel engine, and for each supply, controlling the first actuator to achieve an injection timing of a predetermined angle before top dead centre, controlling the second actuator to achieve a predetermined fuel flow and controlling the third actuator to achieve a predetermined diesel fuel ignition delay by varying the compression ratio of the engine;
 (d) determining the cetane number of the third supply by linear interpolation of the pre-chamber plug positions, corresponding with the respective compression ratio values, for the three supplies; and
 (e) periodically repeating steps (c) and (d) in further cycles to yield a series of cetane number values of the third supply.

The present invention further provides an apparatus for measuring the cetane number of a diesel fuel, the apparatus comprising a diesel engine having a fuel supply system for selectively supplying at least three diesel fuels to the engine, a first actuator for varying the injection timing of the engine, a second actuator for varying the fuel flow into the engine, and a third actuator for varying the compression ratio of the engine, the third actuator comprising a motor for displacing a pre-chamber plug of the engine.

The present invention yet further provides an apparatus for blending a diesel fuel, the apparatus comprising a diesel fuel blending system having at least one supply conduit for a plurality of diesel fuel components and additives, a diesel fuel outlet for the blend and a control system for controlling the composition of the components and additives in the blend, a diesel engine, a fuel supply system for the diesel engine, the fuel supply system being connected to the diesel fuel outlet and to two supplies of diesel fuels of known different cetane numbers, a first actuator for varying the injection timing of the engine, a second actuator for varying the fuel flow into the engine, a third actuator for varying the compression ratio of the engine, the third actuator comprising a motor for displacing a pre-chamber plug of the engine and a processing device for calculating the cetane number of the blended diesel fuel by comparison with the cetane numbers of the two supplies.

The present invention still further provides a method of blending a diesel fuel, the method comprising the steps of:
 (a) providing a diesel engine having means for selectively supplying at least three diesel fuels to the engine, a first actuator for varying the injection timing of the engine, a second actuator for varying the fuel flow of the engine, and a third actuator for varying the compression ratio of the engine;
 (b) providing a first supply of a diesel fuel of known cetane number, a second supply of a diesel fuel of different known cetane number and a third supply of a diesel fuel of unknown cetane number to be measured, the third supply being connected to a diesel fuel blending system to which is supplied a plurality of diesel fuel components and additives in amounts selected to achieve a target value for the cetane number of the blended fuel;
 (c) in a first cycle selectively and alternately supplying the first, second and third supplies to the diesel engine, and for each supply controlling the first actuator to achieve an injection timing of a predetermined angle before top dead centre, controlling the second actuator to achieve a predetermined fuel flow, and controlling the third actuator to achieve a predetermined diesel fuel ignition delay by varying the compression ratio of the engine;

(d) determining the cetane number of the third supply by linear interpolation of the pre-chamber plug positions, corresponding with the respective compression ratio values, for the three supplies;

(e) periodically repeating steps (c) and (d) in further cycles to yield a series of cetane number values of the third supply; and (f) calculating an average cetane number value of the blend.

The present invention can thus provide for the first time the automatic on-line measurement of the cetane number of a diesel fuel in accordance with the accepted standard (ASTM D-613), in particular during the blending process.

BRIEF DESCRIPTION OF THE DRAWINGS

Embodiments of the present invention will now be described, by way of example only, with reference to the accompanying drawings, in which:

FIGS. 1A and 1B are a schematic diagram of an installation for determining the cetane number of a diesel fuel in accordance with a first embodiment of the present invention;

FIG. 2 is a graph showing the sequence of fuel injections into the engine with respect to time;

FIGS. 3A and 3B together comprise a general flow chart of a program of a programmable logic controller (PLC) describing all the sequences from the start of a diesel fuel batch blend until its end;

FIGS. 4A and 4B together comprise a detailed flow chart of one step of the general flow chart shown in FIG. 3, describing the subsequence of actions successively done on each fuel;

DETAILED DESCRIPTION OF THE PREFERRED EMBODIMENTS

Figure 1A:
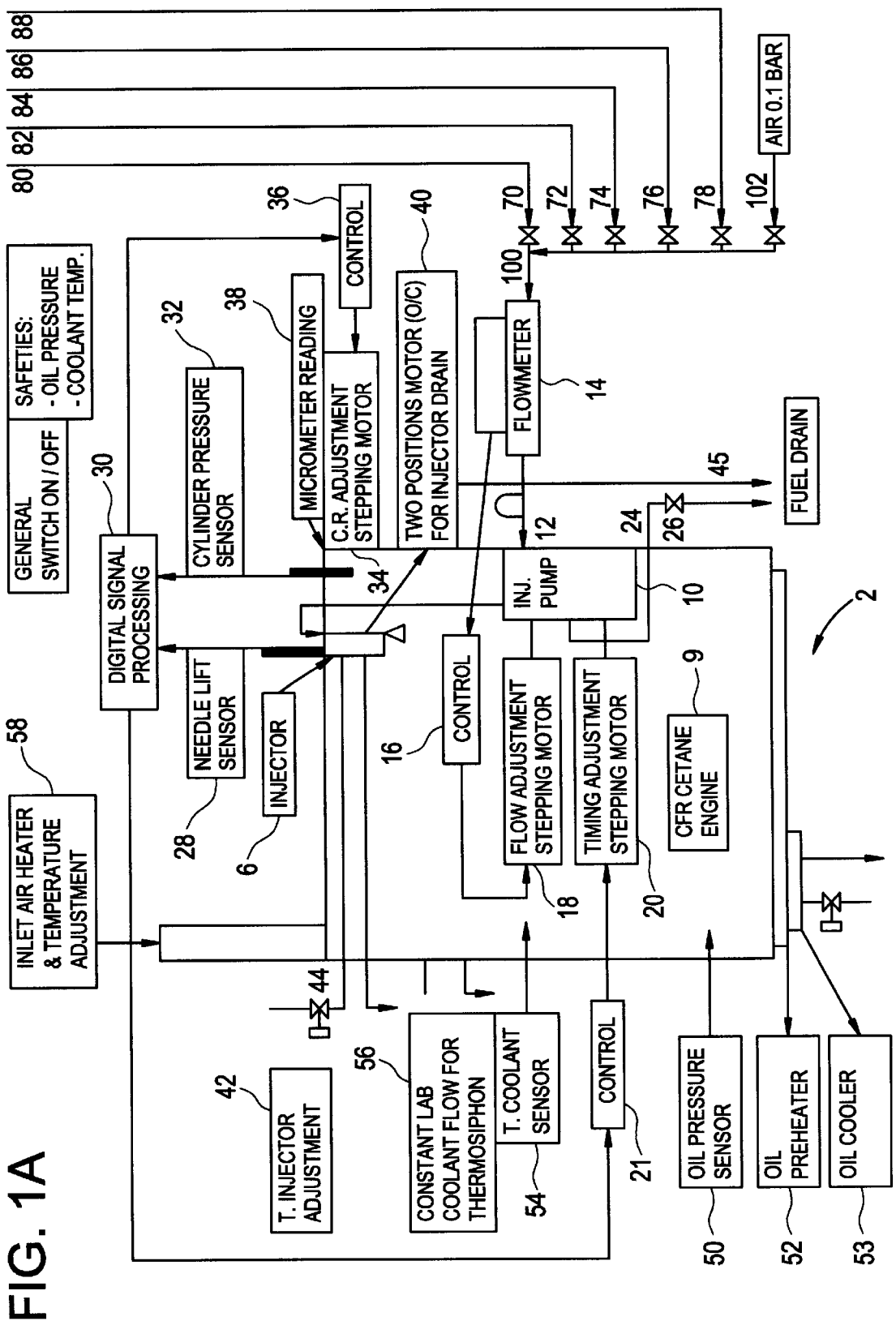

Referring to FIGS. 1A and 1B, there is shown a schematic representation of an installation, designated as a whole as 2, for the on-line determination of the cetane number of a diesel fuel.

The installation 2 comprises a single cylinder four stroke diesel cetane engine 4, the mechanical details of which, such as the piston, cylinder, crankshaft, etc., are not shown in FIGS. 1A and 1B. The engine 4 is the CFR engine referred to hereinabove.

The engine 4 is provided with an injector 6 for injecting diesel fuel into the single cylinder (not shown). The injector 6 is connected via a fuel line 8 to an injection pump 10 which is in turn connected via a further fuel line 12 to a flow meter 14. The flow meter communicates with an array of parallel fuel inlet valves 70, 72, 74, 76, 78 each associated with a respective parallel fuel line 80, 82, 84, 86, 88, each of which respectively communicates with a supply of a particular fuel, designated generally as fuel supplies 90, 92, 94, 96, 98.

The fuel lines downstream of the valves 70, 72, 74, 76, 78 converge to form a single fuel input line 100 for the flow meter 14. The single fuel input line 100 is also connected via a valve 102 with compressed air, typically at a pressure of around 0.1 bar, to drain the current fuel before switching to the next fuel.

The delivery of diesel fuel into the single cylinder is controlled by a fuel control 16, which receives a signal from the flow meter 14 and controls the operation of the injection pump 10 with the flow adjustment stepping motor 18.

The injection timing adjustment is controlled by a control 21, which receives a signal from a digital signal processing unit 30 and controls the operation of the injection pump 10 with an injection timing adjustment stepping motor 20.

The flow adjustment stepping motor 18 and the injection timing adjustment stepping motor 20 are required because of the variations in the viscosity of the fuels.

The injection pump 10 is provided with a fuel drain 24, with a downstream valve 26, for draining the fuel from the injection pump 10, the flow meter 14 and the fuel lines 12 and 100.

The injector 6 is equipped with a two positions motor 40, opening and closing the injection line drain, for draining the high pressure part of the injection system via the fuel drain 45.

The injector temperature is controlled by an adjuster 42 via the coolant flow with a proportional cooling valve 44.

The first fuel supply 90 is a supply of a check diesel fuel. The check diesel fuel typically comprises a source of chemical products, which in accordance with ASTM D-613 is supplied by Phillips Petroleum, which is employed for calibrating the installation at the start of a batch blending.

The diesel fuels supplies 92, 94, 96 respectively comprise reference fuels having low, medium and high known cetane numbers. These reference fuels typically have cetane numbers of 44, 49.5 and 55. The reference fuels are refinery products comprising manufactured diesel fuels which have been round robin tested by about 20 to 25 different manual CFR cetane engines in a correlation exercise organised by the Institut Français du Pétrole. Each fuel has been tested to determine its cetane number using the known procedure of ASTM D-613 by a number of different CFR cetane number engines.

That known test, as specified above, has a reproducibility of only 3.9 cetane points. If the fuel is round robin tested, by for example 20 testers, then the reproducibility of the average cetane number from those tests, used as a true value, and found for each reference fuel in the round robin test, is $3.9/\sqrt{20}$, i.e. approximately 0.9 cetane points. Thus the three reference fuels of low, medium and high cetane number have relatively accurately determined cetane numbers as a result of the round robin testing.

Also, unlike the known batch processes using ASTM D-613 for measuring cetane numbers, the reference fuels are refinery products, as opposed to blends of chemical products which have been produced to simulate refinery diesel fuels. The cetane range bridging the low, medium and high reference fuels is around 11 cetane points. This range encompasses two adjacent ranges of 5.5 cetane points over which valid cetane numbers can be determined in accordance with the ASTM D-613 procedure. The three reference fuels have cetane numbers which comply with the requirements specified in ASTM D-613 of a maximum allowed difference of 5.5 cetane points between bracketing reference fuels.

The last fuel supply 98 is the blended fuel supply 98 which is connected to the diesel fuel blending system (not shown) so that the apparatus 2 can sequentially measure the cetane number of the blended fuel from the blender on an on-line basis.

The determination of injection timing and combustion start are done by digital processing of the signals of respectively the injector needle lift sensor 28 and the cylinder pressure sensor 32 under control of a digital signal processing unit 30.

The tuning of the compression ratio in the single cylinder is achieved by the displacement of the pre-chamber plug (not shown). There is accordingly provided a stepping motor 34 for the compression ratio adjustment which in turn acts to displace the pre-chamber plug (not shown). The stepping motor 34 is in turn controlled by control 36 which is informed by the digital signal processing unit 30.

A micrometer 38 is provided for giving a reading of the pre-chamber plug position.

A programmable logic controller (PLC) (not shown) controls the whole installation. The PLC includes the fuel control 16, the control 21 for the injection timing adjustment and the control 36 for the stepping motor 34. The digital signal processing unit 30 communicates its calculation results to the PLC, to control the injection timing stepping motor 20 and the compression ratio stepping motor 34 via its controls 21 and 36.

The PLC also continuously checks the engine conditions with an oil pressure sensor 50, a coolant temperature sensor 54, an inlet air temperature sensor (not shown) and an injector coolant temperature sensor (not shown). The PLC maintains the engine in the conditions required by the ASTM D-613, by controlling with an oil pre-heater 52, an oil cooler 53, a coolant flow control 56, an inlet air heater 58 and an injector cooler 42. The PLC also starts the installation and stops it in case of insufficient oil pressure and/or excessive coolant temperature. Finally, the PLC controls the different on/off valves 26,70,72,74,76,78,102 and the three engine adjustment stepping motors 18,20,34, following the sequence of the ASTM D-613 procedure described further. Most importantly, the PLC calculates the cetane number and communicates the calculated number to the blend controller as described hereinbelow.

In the testing method, the position of the compression plug in the pre-chamber, for tuning the compression ratio in the engine to achieve a constant ignition delay of 13° crank angle, is measured for the various cetane numbers fuels. The flow adjustment stepping motor 18 and the injection timing adjustment stepping motor 20 are required because of the variations in the viscosity of the fuels.

Figure 4B:
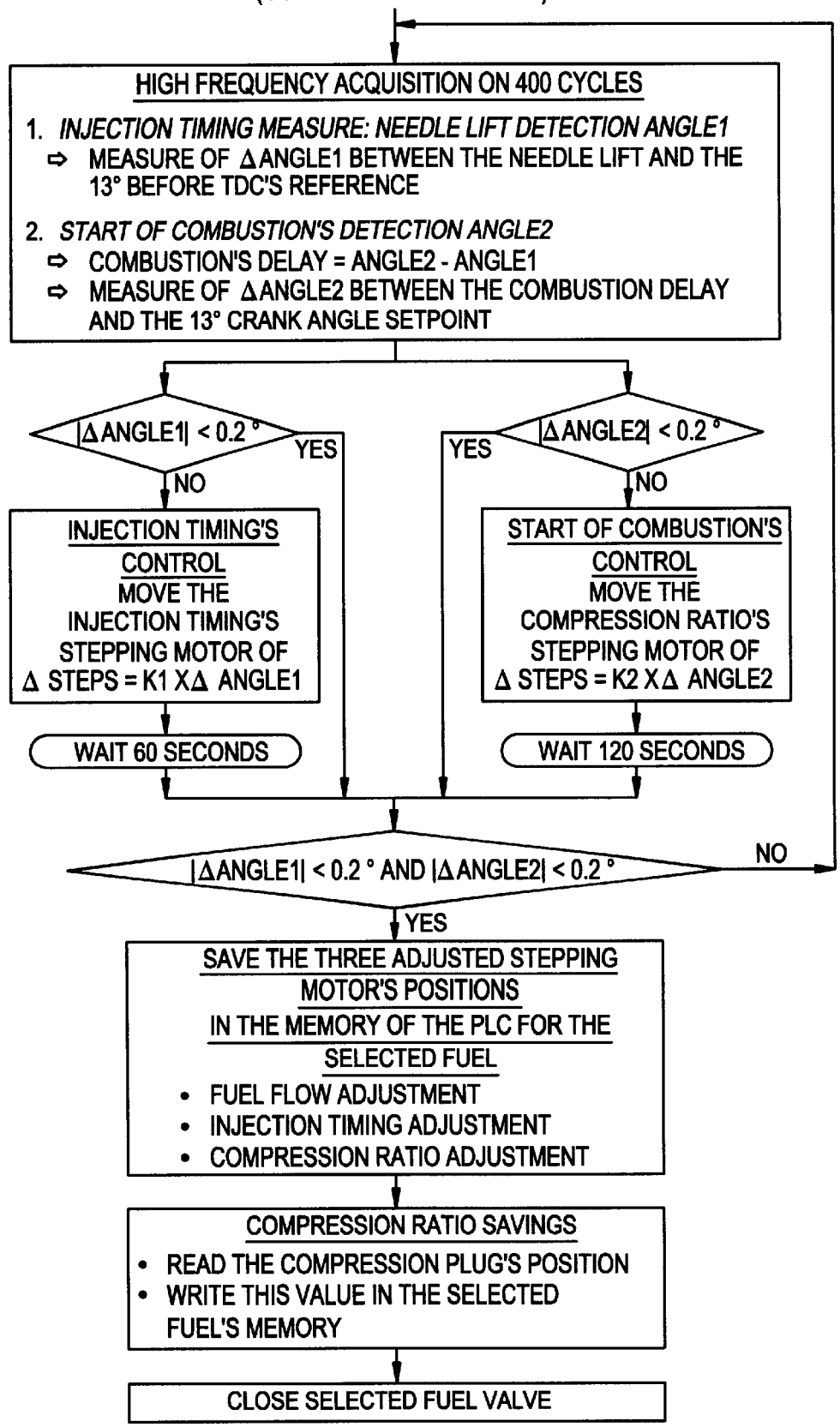

FIGS. 4A and 4B show a flow chart for the automatic sequenced adjustment of the quantity of injected fuel, of the injection timing and of the compression ratio of the engine with one selected fuel, in order to stabilize the engine in the conditions required by the ASTM D-613.

At each fuel change, the fuel pump is rinsed, the injector is drained and the three stepping motors are set initially to their last adjusted position corresponding to the same fuel used in an earlier cycle. After the 3minutes engine stabilisation time prescribed by the ASTM D-613, the fuel flow is measured by the flow meter and eventually corrected with the fuel flow adjustment stepping motor 20, to be around 13 ml per minute.

The digital signal processing unit 30 determines the injection timing and the ignition delay. The injection timing is eventually adjusted to 13° before top dead centre with the stepping motor 18.

Finally, when the injection timing is tuned, the compression ratio adjustment stepping motor 34 is eventually adjusted, to achieve the ignition delay of 13°.

When the engine is stabilised in the conditions required by the ASTM D-613, the compression plug position is measured and saved in the memory of the PLC for the corresponding fuel for a subsequent blend fuel cetane number determination. The positions of the three adjustment stepping motors 18,20,34 are also saved in the memory of the PLC as next pre-set positions for the same fuel.

As may be seen from FIG. 2, initially the first reference fuel is injected and tested. Then a process sample of the blend fuel is tested and following that test the second reference fuel is tested. The determination of injection timing and combustion start are done by digital processing of the signals of respectively the injector needle lift sensor 28 and the cylinder pressure sensor 32 under control of the digital signal processing unit 30. The average needle lift and cylinder pressure are determined for 400 consecutive cycles. These measurements take a period of approximately 1 minute. The injection duration of each fuel is about 4 minutes, if the stepping motors pre-set positions do not require adjustment (most of the time). As may be seen from FIG. 2, the sequence of fuels is reference 1, blend fuel, reference 2, reference 1, reference 2, blend fuel, which is the order prescribed by the ASTM-D613 standard. The cetane number of the blend fuel is determined before each supply of the first reference fuel. This provides a cyclic determination of the blend fuel cetane number value, typically about every 12 minutes.

Figure 3A:
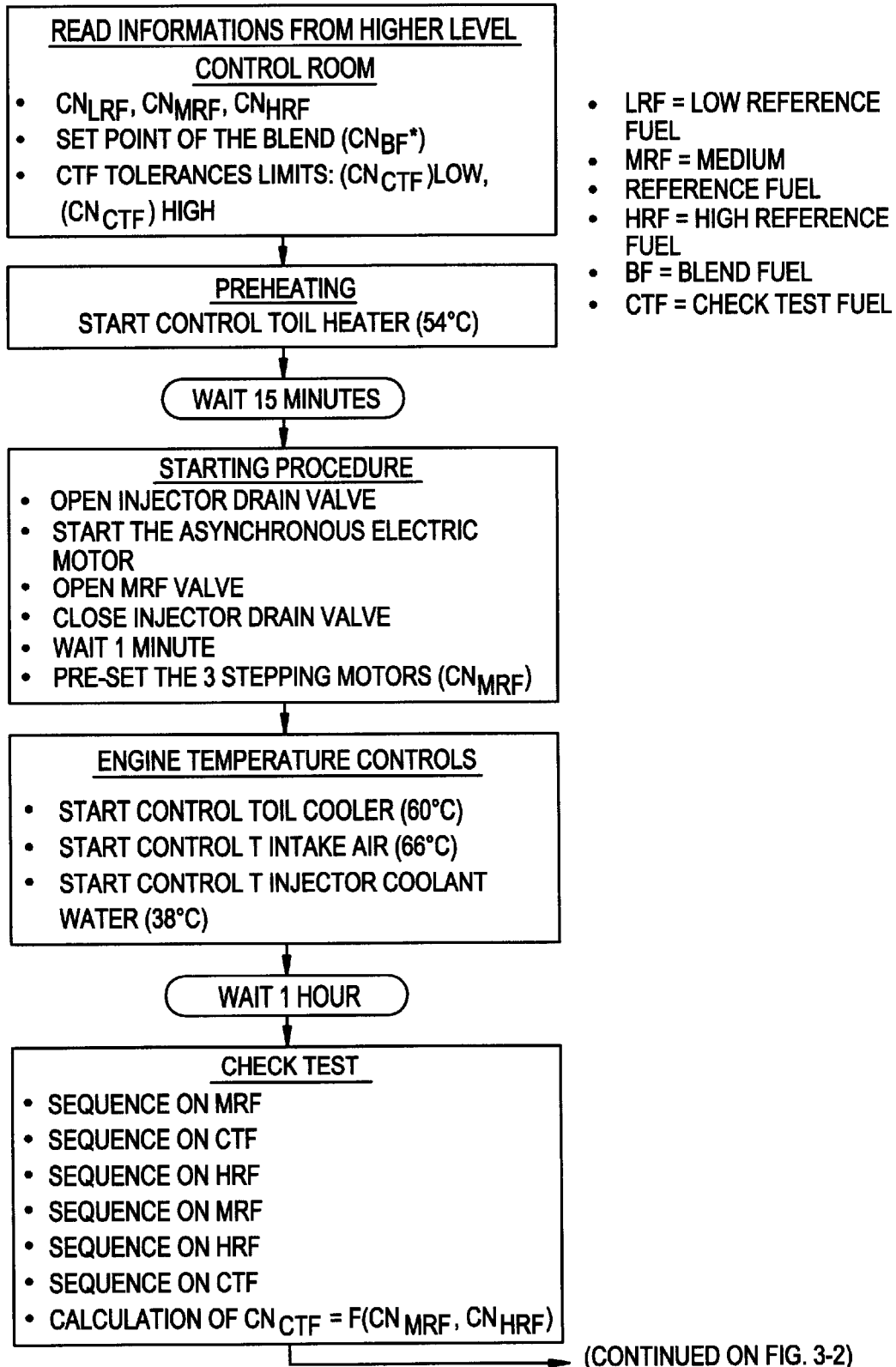

FIGS. 3A and 3B show a flowchart describing the complete operating sequence required for the automatic on-line determination of the cetane number of a blend fuel, according to the sequence shown in FIG. 2.

Before starting the blend fuel cetane number determination procedure, the engine must pass a check test. The check fuel is submitted to the sequence specified in FIGS. 4A and 4B, and thereafter the same sequence is performed successively on two bracketing reference fuels with cetane numbers known from round robin testing. Then, the check fuel cetane number, calculated by linear interpolation of the compression plug position found for the check fuel between the positions found for the two bracketing reference fuels, is compared with the check fuel true cetane number and its tolerances.

If the installation passes the check test, the on-line blend fuel cetane number determination is started.

As described hereinabove with reference to the check fuel, the medium reference fuel is submitted to the sequence specified in FIGS. 4A and 4B, and thereafter the same sequence is performed alternately on the blend fuel and on the other reference fuel.

The two bracketing reference fuels are the low and medium cetane number references fuels if the blend fuel cetane number set point, communicated by the refinery, is less than that of the medium reference fuel. If the blend fuel cetane number set point is higher than that of the medium reference fuel, then the two bracketing reference fuels are the medium and high cetane number references fuels.

The blend fuel cetane number is then calculated by linear interpolation of the compression plug position found for the blend fuel between the positions of the two bracketing reference fuels, which cetane numbers are known from round robin testing.

The cetane number of the blend fuel is stored and recorded for subsequent analysis, for example for on-line feed back control of the cetane number of the blend fuel by changing the additives or components added to the diesel fuel, or by integrating a value of the cetane number of the fuel for certification purposes.

This sequence of continual testing is, as shown in FIG. 2, repeated sequentially during the blending process. At the end of the blending process, the engine is stopped as specified at the end of FIG. 3B.

Thus the method and installation of the present invention enable continuous monitoring of blended fuel cetane number during the blending. This continuous monitoring can be used for closed loop control of the blend ratios. In other words, the cetane numbers may be used continuously to adjust the cetane number of the composition to the desired target value.

Moreover, the cetane numbers which are continually measured during the blending process may be integrated to provide a single value of the cetane number of the complete batch; which can be used to certify the cetane number of the batch in accordance with ASTM D-613.

If the batch flow evolution is known, the certification cetane number can be calculated as weighted average of all the calculated cetane number values.

The method and installation of the invention determine the cetane number of a blended fuel automatically and continually on-line during the blending process almost fully in accordance with ASTM D-613, except for the reference fuels which are round robin tested refinery products, corresponding to the "standard fuels" used in the procedures of ASTM D-2885 for on-line automatic octane number determination. This procedure enables the refinery to use the result of the batch integration as a certified ASTM D-613 cetane number of the whole batch, calculated with a much higher precision than the single manual measurement on the finished blend as employed in the prior art.

The present invention has industrial application in refineries which diesel fuel blend system, in particular in countries where the cetane number of the fuel needs to be certified, in agreement with the current The present invention will now be described further with reference to the following non-limiting Example.

EXAMPLE

Figure 6:
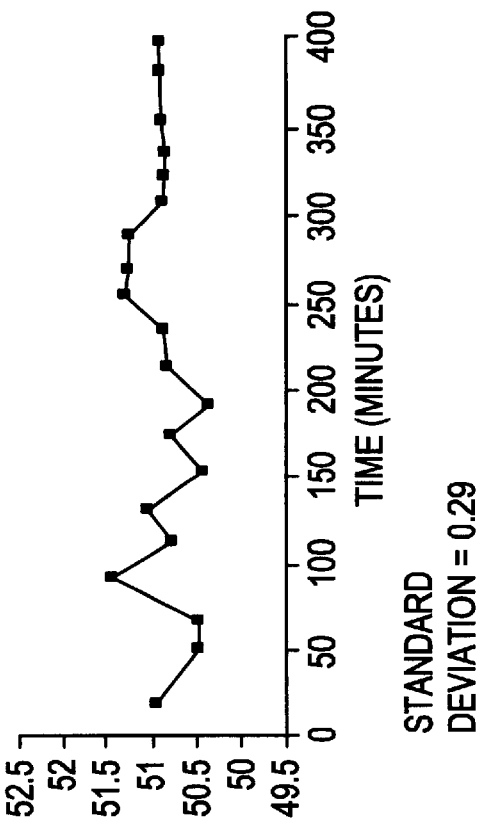
FIG. 6 is a graph showing the relationship between the test fuel cetane number calculated by linear interpolation of the compression plug position found for the test fuel between the positions found for two bracketing reference fuels and time in accordance with the example.
Figure 5:
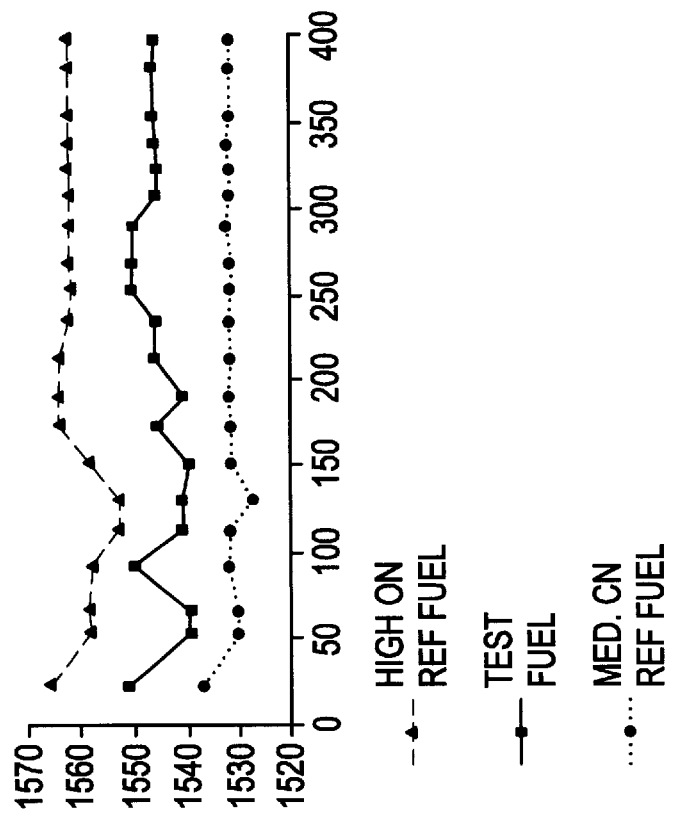
FIG. 5 is a graph showing the pre-chamber plug position for the two known cetane number reference fuels and for a constant test fuel with respect to time in accordance with one example of the invention.

The method as described herein with reference to FIGS. 1A to 4B was carried out using two known cetane number reference fuel having a cetane number of 52.3. The cetane number testing method was performed using the apparatus of FIGS. 1A and 1B and using the sequences of FIGS. 2 to 4B. FIG. 5 represents a graph showing the pre-chamber plug position (in micrometers) for the two known cetane number reference fuels (medium and high) and for a constant test fuel with respect to time. The test fuel cetane number was calculated by linear interpolation of the compression plug position found for the test fuel between the positions found for the two bracketing reference fuels. FIG. 6 is a graph showing the calculated cetane number and its variation with time.

It may be seen from FIG. 6 that the standard deviation of the standard cetane number determination is 0.29 and that the repeatability of the single interpolations is thus 0.8 cetane points. This value has to be compared with the repeatability of the ASTM procedure which is $0.9 \times \sqrt{2}$ cetane points, as the ASTM D-613 procedure prescribes as a single test the average of two interpolations done on the same three products. This yields a repeatability of 1.3 cetane points using the normal ASTM D-613 procedure. This is higher than the 0.8 points repeatability for a single interpolation which is achieved in accordance with the method of the invention. Thus the method of invention clearly provides an improved repeatability of the cetane number determination.

As may be seen from FIG. 6, the average of the cetane number determination ($\overline{CN}$) is 50.85. From FIG. 5 it may be seen that the theoretical cetane number ($CN_{th}$) of a 50/50 blend of the high cetane number and medium cetane number reference fuels is (52.3+49.6)/2 i.e. 50.95. The difference between this average ($\overline{CN}$) and the theoretical cetane number ($CN_{th}$) of a 50/50 blend of the high reference and medium reference fuels is thus 0.1. This difference is within the normal spread of repeatability, r, i.e.

$$r[(\overline{CN}-CN_{th})=r\ \overline{CN}+0=0.8/\sqrt{20}=0.18,$$

where 20 is the number of cetane number calculations in FIG. 5. The average of 20 cetane number determinations is thus a reliable figure for the theoretical cetane number of the 50/50 blend between the high CN and medium CN reference fuels.

What is claimed is:

1. A method of continually measuring the cetane number of a diesel fuel, the method comprising the steps of:

(a) providing a diesel engine having means for selectively supplying at least three diesel fuels to the engine, a first actuator comprising a first stepping motor for an injection timing adjustment of the engine for varying the injection timing of the engine, a second actuator comprising a second stepping motor for a fuel flow adjustment device of the engine for varying the fuel flow of the engine, and a third actuator comprising a third stepping motor for displacing a pre-chamber plug of the engine for varying the compression ratio of the engine;

(b) providing a first supply of a diesel fuel of known cetane number, a second supply of a diesel fuel of different known cetane number and a third supply of a diesel fuel of unknown cetane number to be measured, the third supply being connected to a diesel fuel blending system;

(c) in a first cycle selectively and alternately supplying the first, second and third supplies to the diesel engine, and for each supply, controlling the first actuator to achieve an injection timing of a predetermined angle before top dead centre, controlling the second actuator to achieve a predetermined fuel flow and controlling the third actuator to achieve a predetermined diesel fuel ignition delay by varying the compression ratio of the engine;

(d) determining the cetane number of the third supply by linear interpolation of the pre-chamber plug positions, corresponding with the respective compression ratio values, for the three supplies;

(e) periodically repeating steps (c) and (d) in further cycles to yield a series of cetane number values of the third supply; and (f) continually feeding the cetane number values obtained in step (e) fed back to a control system for the diesel fuel blending system thereby to control the composition of the third supply of diesel fuel to achieve a desired cetane number of said third supply of diesel fuel.

2. A method according to claim 1 wherein in each cycle the diesel fuels are supplied to the engine in step (c) in a sequence comprising the first supply, the third supply, the second supply and the third supply.

3. A method according to claim 1 wherein the cetane number is determined in step (d) after supplying each of the first and second supplies to the engine.

4. A method according to claim 1 wherein the cetane number of the third supply is within a cetane number range defined between the different cetane numbers of the first and second supplies.

5. A method according to claim 4 wherein at least four diesel fuels are selectively supplied to the engine, the at least four diesel fuels including the third supply and three different diesel fuels each of known different cetane numbers which define two contiguous cetane number ranges, the first and second supplies being selected from the three different diesel fuels thereby to encompass the cetane number of the third supply within a respective one of the two cetane number ranges.

6. A method according to claim 1 wherein each supply of known cetane number has been tested to determine its cetane number by a plurality of separately performed tests in different engines and the known cetane number has been determined as an average value from the tests.

7. A method according to claim 6 wherein each supply of known cetane number has been tested to determine its cetane number by at least twenty separately performed tests in different engines.

8. A method according to claim 1 wherein the diesel engine is calibrated prior to step (c) with a supply of a check diesel fuel of known cetane value.

9. A method according to claim 1 wherein the series of cetane number values obtained in step (e) is integrated to yield an average cetane number value for a batch of the third supply of diesel fuel.

10. An apparatus for measuring the cetane number of a diesel fuel, the apparatus comprising a diesel engine having a fuel supply system for selectively supplying at least three diesel fuels to the engine, a first actuator for varying the injection timing of the engine, a second actuator for varying the fuel flow into the engine, and a third actuator for varying the compression ratio of the engine, the third actuator comprising a motor for displacing a pre-chamber plug of the engine.

11. An apparatus according to claim 10 wherein the first actuator is a stepping motor for a timing adjustment device of the engine.

12. An apparatus according to claim 10 wherein the third actuator is a stepping motor.

13. An apparatus according to claim 10 wherein the second actuator is a stepping motor for a fuel flow adjustment device of the engine.

14. An apparatus according to claim 10 wherein the fuel supply system includes a fuel injection pump for pumping fuel into a cylinder of the diesel engine, a flow meter for measuring the flow of fuel to the injection pump, and an array of fuel inlet valves, each connected on a downstream side with respect to fuel flow to the flow meter and on an upstream side to a respective fuel line.

15. An apparatus for blending a diesel fuel, the apparatus comprising a diesel fuel blending system having at least one supply conduit for a plurality of diesel fuel components and additives, a diesel fuel outlet for the blend and a control system for controlling the composition of the components and additives in the blend, a diesel engine, a fuel supply system for the diesel engine, the fuel supply system being connected to the diesel fuel outlet and to two supplies of diesel fuels of known cetane numbers, a first actuator for varying the injection timing of the engine, a second actuator for varying the fuel flow into the engine, a third actuator for varying the compression ratio of the engine, the third actuator comprising a motor for displacing a pre-chamber plug of the engine and a processing device for calculating the cetane number of the blended diesel fuel by comparison with the cetane numbers of the two supplies through linear interpolation of the pre-chamber plug positions necessary to achieve a predetermined diesel fuel ignition delay.

16. An apparatus according to claim 15 wherein the processing device comprise a program to calculate the cetane number of the blended diesel fuel a plurality of times and to calculate an average cetane number value for the blend.

17. An apparatus according to claim 15 wherein the processing device comprises a program to send an input to the control system thereby periodically varying the composition of the blend.

18. A method of blending a diesel fuel, the method comprising the steps of:

(a) providing a diesel engine having means for selectively supplying at least three diesel fuels to the engine, a first actuator for varying the injection timing of the engine, a second actuator for varying the fuel flow of the engine, and a third actuator for varying the compression ratio of the engine;

(b) providing a first supply of a diesel fuel of known cetane number, a second supply of a diesel fuel of different known cetane number and a third supply of a diesel fuel of unknown cetane number to be measured, the third supply being connected to a diesel fuel blending system to which is supplied a plurality of diesel fuel components and additives in amounts selected to achieve a target value for the cetane number of the blended fuel;

(c) in a first cycle selectively and alternately supplying the first, second and third supplies to the diesel engine, and for each supply controlling the first actuator to achieve an injection timing of a predetermined angle before top dead centre, controlling the second actuator to achieve a predetermined fuel flow, and controlling the third actuator to achieve a predetermined diesel fuel ignition delay by varying the compression ratio of the engine;

(d) determining the cetane number of the third supply by linear interpolation of the pre-chamber plug positions, corresponding with the respective compression ratio values, for the three supplies;

(e) periodically repeating steps (c) and (d) in further cycles to yield a series of cetane number values of the third supply; and (f) calculating an average cetane number value of the blend.

19. A method according to claim 18 further comprising certifying the average cetane number value in accordance with the provisions of ASTM D-613.

20. A method according to claim 18 further comprising the step of:

(g) feeding back the series of cetane numbers to a control system for the diesel fuel blending system thereby to control the composition of diesel fuel components and additives in the blend to achieve the target value for the cetane number.

\* \* \* \* \*

UNITED STATES PATENT AND TRADEMARK OFFICE
CERTIFICATE OF CORRECTION

PATENT NO. : 6,609,413 B1
DATED : August 26, 2003
INVENTOR(S) : Roger De Craecker It is certified that error appears in the above-identified patent and that said Letters Patent is hereby corrected as shown below:

Column 9,
Line 34, add -- industry specifications. -- after "current".

Signed and Sealed this

Fifth Day of October, 2004

JON W. DUDAS
*Director of the United States Patent and Trademark Office*